(12) United States Patent
Sato et al.

(10) Patent No.: US 8,900,647 B2
(45) Date of Patent: Dec. 2, 2014

(54) *KOJI* MOLD HAVING LARGE-SCALE GENOMIC DUPLICATION

(75) Inventors: Atsushi Sato, Noda (JP); Yoshiki Hanya, Noda (JP)

(73) Assignee: Kikkoman Corporation, Chiba (JP)

(*) Notice: Subject to any disclaimer, the term of this patent is extended or adjusted under 35 U.S.C. 154(b) by 0 days.

(21) Appl. No.: 13/120,966

(22) PCT Filed: Apr. 16, 2010

(86) PCT No.: PCT/JP2010/056880
§ 371 (c)(1),
(2), (4) Date: Apr. 20, 2011

(87) PCT Pub. No.: WO2010/119967
PCT Pub. Date: Oct. 21, 2010

(65) Prior Publication Data
US 2012/0027910 A1 Feb. 2, 2012

(30) Foreign Application Priority Data

Apr. 17, 2009 (JP) ................ P2009-100645

(51) Int. Cl.
| | | |
|---|---|---|
| A23L 1/23 | (2006.01) | |
| A23L 1/227 | (2006.01) | |
| A23L 1/238 | (2006.01) | |
| C12R 1/66 | (2006.01) | |
| C12R 1/69 | (2006.01) | |
| C12N 9/30 | (2006.01) | |
| C12N 9/62 | (2006.01) | |
| C12N 15/52 | (2006.01) | |
| A23L 2/84 | (2006.01) | |
| C12N 9/58 | (2006.01) | |

(52) U.S. Cl.
CPC .......... *A23L 1/238* (2013.01); *C12N 15/52* (2013.01); *A23L 2/84* (2013.01); *C12N 9/58* (2013.01); *C12R 1/66* (2013.01); *C12R 1/69* (2013.01); *C12N 9/242* (2013.01); *C12N 9/62* (2013.01); *C12Y 302/01001* (2013.01)
USPC ............. 426/60; 426/589; 435/256.1

(58) Field of Classification Search
CPC ........................ C12N 15/52; A23L 1/238
USPC ..................... 426/589; 435/256.1
See application file for complete search history.

(56) References Cited

U.S. PATENT DOCUMENTS 6,090,607 A * 7/2000 Van Den Broek et al. .... 435/223
6,830,905 B2 * 12/2004 Koibuchi et al. ............ 435/110

FOREIGN PATENT DOCUMENTS

| | | |
|---|---|---|
| CN | 1884476 | 12/2006 |
| EP | 1132461 A1 * | 9/2001 |
| JP | 57-174087 | 10/1982 |
| JP | 6-153896 | 6/1994 |
| JP | 7-222584 | 8/1995 |
| JP | 7-274944 | 10/1995 |
| JP | 9-70287 | 3/1997 |
| JP | 10-210967 | 8/1998 |
| JP | 2007-228849 | 9/2007 |
| JP | 2008-54580 | 3/2008 |
| JP | 2008-306991 | 12/2008 |

OTHER PUBLICATIONS

Smith C. A., et al., Silencing of the aflatoxin gene cluster in a diploid strain of *Aspergillus flavus* is suppressed by ectopic aflR expression, Genetics, 2007, 176(4), p. 2077-2086, and pp. 3-15 of Supplemental Table S2.
Kalayanamitr A., et al., Occurrence of toxicity among protease, amylase, and color mutants of a nontoxic soy sauce *koji* mold, Appl. Environ. Microbiol., 1987, 53(8), p. 1980-1982.
International Search Report for PCT/JP2010/056880 dated Jun. 22, 2010.
Machida M., et al., Genome sequencing and analysis of *Aspergillus oryzae*, Nature, vol. 438, 1157-1161, 2005.
Amsal A., et al., Increased digestibility of raw starches by mutant strains of *Aspergillus awamori*, Food Sci. Technol. Res., 5(2), 153-155, 1999.
Chinese Office Action dated Aug. 21, 2012, from the Chinese Patent Office in corresponding Chinese Application No. 201080002739.6, and English translation thereof.
Smith, C. et al., Silencing of the Aflatoxin Gene Cluster in a Diploid Strain of *Aspergillus flavus* Is Suppressed by Ectopic aflR Exression, Genetics, 2007, vol. 176, No. 4, pp. 2077-2086.
Database WPI, Week 198248, Thomson Scientific, London, GB; AN 1982-03726J & JP S57174087 A (Higeta Shoyu KK) Oct. 26, 1982.
Database FSTA [Online], International Food Information Service (IFIS), Frankfurtmain, DE; Yokoyama, T. et al: Breeding *koji* mould by a combination of mutation and diploidization (translated), Database accession No. FS-1984-04-T-0223; & vol. 9, No. 4 , p. 137, XP009174806, Journal of the Japan Soy Sauce Research Institute [Nihon Shoyu Kenkujo Zasshi] 1983.
Database WPI, Week 198545, Thomson Scientific, London, GB; AN 1985-279140 & JP S60 188057 A (Kikkoman Corp) Sep. 25, 1985.

(Continued)

*Primary Examiner* — Jyoti Chawla
(74) *Attorney, Agent, or Firm* — Roylance, Abrams, Berdo & Goodman, L.L.P.

(57) ABSTRACT

The purpose of the present invention is to breed a koji mold, which has improved capability of producing a variety of industrially applicable enzymes, without using the genetic recombination technology. By mutagenizing a strain belonging to the genus *Aspergillus*, a strain having a duplication of a large-scale genome region of 900 kb or more and is able to produce a variety of enzymes required in manufacturing soy sauce, for example, protease, etc. was obtained. This strain enables efficient production of various foods such as soy sauce.

19 Claims, 11 Drawing Sheets

(56) References Cited

OTHER PUBLICATIONS

Database WPI, Week 200943, Thomson Scientific, London, GB; AN 2009-K99582 & JP 2009 095279 A (Dokuritsu Gyosei Hojin Nippon Gakujutsu) May 7, 2009.

Kalayanamitr, A. et al., Occurrence of toxicity among protease, amylase, and color mutants of a nontoxic soy sauce *koji* mold, Applied and Environmental Microbiology, 1987, vol. 53, No. 8, pp. 1980-1982.

Pettersson, M. et al., Evolution of new gene functions: simulation and analysis of the amplification model, Genetics, 2008, vol. 135, No. 3, pp. 309-324.

Koszul, R., Stability of Large Segmental Duplications in the Yeast Genome, Genetics, 2005, vol. 172, No. 4, pp. 2211-2222.

Parag, Y. et al., Genetic Control of Chromosome Instability in *Aspergillus-nidulans* as a Mean for Gene Amplification in Eukaryotic Microorganisms, Molecular and General Genetics, 1975, vol. 140, No. 4, pp. 275-287.

Database WPI, Week 201027, Thomson Scientific, London, GB; AN 2010-D91158 & JP 2010 075131 A (Yamasa Shoyu KK) Apr. 8, 2010.

Extended European Search Report for EP Appln. No. 10 764 549.1, dated Jan. 2, 2014.

\* cited by examiner

KOJI MOLD HAVING LARGE-SCALE GENOMIC DUPLICATION

TECHNICAL FIELD

The present invention relates to a koji mold having a duplication of a large-scale genomic region of 900 kb or more, and so on.

BACKGROUND ART

Enzymes produced by koji molds have been used in a diversity of industries.

For example, various enzymes produced by koji molds have been utilized in producing soy sauce which is a traditional food in Japan. To produce soy sauce, a koji mold is grown in soybeans and wheat, which are the starting materials, and allowed to produce various enzymes. These enzymes produced by the koji mold decompose proteins, saccharides, lipids and so on and promote lactic acid fermentation and yeast fermentation in the subsequent steps. When the koji mold produces a large amount of enzymes which decompose the starting materials during the process, the utilization efficiency of the starting materials and compression level can be improved to largely enhance the productivity. Additionally, since a sufficient amount of substrates to the lactic acid fermentation and yeast fermentation is provided, the fermentations are appropriately conducted. Thus, the qualities of soy sauce are highly improved.

Accordingly, it is very important from an industrial standpoint to breed koji molds having high enzyme productivity. For this purpose, breedings have been energetically conducted so far. Since the entire genome sequence of *Aspergillus oryzae* RIB40 was identified (Non-Patent Document 1), this strain becomes applicable to breeding.

Methods for breeding koji molds with a purpose of high enzyme productivity are roughly classified into the mutation method and the genetic recombination method.

The genetic recombination method comprises introducing a target gene into a koji mold with the use of transformation to breed the transformant. Usually, genes of 5 to 6 kb in size are introduced by the method. Introduction of a gene of 10 kb or larger is very difficult to succeed because of a considerable decrease in the transformation efficiency. Additionally, the region to be introduced includes the promoter region, structural gene region or terminator region of the target gene or, in some cases, a gene which can serve as a marker in screening. Thus, it is difficult to introduce multiple genes in a fragment of 10 kb or smaller. Therefore, the genetic recombination method is effective in an industrial field such as enzyme production where it is merely required to highly produce a single enzyme alone while in an industrial field such as food manufacturing where a plural enzymes for decomposing starting materials should be highly produced simultaneously, the genetic recombination method is not effective. In soy sauce manufacturing cited as an example of food manufacturing, it is necessary to produce a large amount of various kinds of enzymes including enzymes decomposing various starting materials for enhancing the yield, various enzymes for enhancing the level of compression, enzymes for enriching the body taste and so on. To highly produce these various kinds of enzymes at the same time by the genetic recombination method, transformation should be repeatedly carried out. For this purpose, it is necessary to construct a system whereby a marker to be used in screening a transformant can be recycled. However, it is extremely difficult to construct such a system. Even supposing that transformation is repeatedly carried out and thus genes of a large variety of enzymes are inserted into genomes, the inserted genes cannot always sufficiently function because of the problems relating to gene loci and expression control systems. Moreover, since the enzyme production mechanisms of koji molds still remain unknown in many points, there is no guarantee that the productivity of a target enzyme can be enhanced merely by inserting a gene.

Additionally, foods manufacturing using gene recombination technology is still unacceptable in the Japanese market. Thus, there are some problems in the application of the genetic recombination method to food manufacturing in practice. Therefore, breedings have been conducted by the mutation method using, for example, ultraviolet light irradiation. However, the method causes an associated mutation other than the target mutation. In the case, therefore, even though a mutant having an enhanced productivity of the desired enzyme can be obtained, there frequently arise some problems such as a slow growth rate, a decrease in the productivity of another enzyme, etc.

Furthermore, a koji mold mutant is genetically unstable in many cases. Namely, it is frequently observed that the property of a mutant becomes identical with that of the parent strain thereof as the mutant grows (hereinafter this phenomenon will be called "reverse mutation"), which brings about troubles in the industrial application.

Accordingly, although a koji mold which highly produces a variety of enzymes simultaneously has been required in industries such as the food industry with a need for various kinds of enzymes at the same time, there are problems as discussed above.

Examples of known methods for breeding a koji mold which highly produce enzymes with the use of the mutation method are as follows: a method which comprises treating *Aspergillus oryzae* RIB128 with N-methyl-N'-nitro-N-nitrosoguanidine (hereinafter referred to as NTG) to obtain a strain having a high phytase activity and reduce the amount of phytin in sake and increase the amount of inositol which is a biologically active substance (Patent Document 1); a method which comprises treating *Aspergillus oryzae* AJ117281 with NTG to obtain a mutant having a high protease activity and produce a nitrogen-rich protein hydrolysate (Patent Document 2); a method which comprises treating *Aspergillus oryzae* AJ117290 (FERMP-14259) with NTG to obtain a mutant having a high glutaminase activity and produce a protein hydrolysate having a high glutamic acid content (Patent Document 3); and so on. With respect to the induction of mutation, examples of agent for the induction of mutation not only include NTG as described above but also other chemicals commonly used such as hydroxylamine, ethylmethylsulfonic acid and the like or irradiation with ultraviolet light, radial ray, X-ray and the like.

Other examples of known breedings using the mutation method include: a method which comprises mutagenizing *Aspergillus oryzae* O-1013 (FERM P-16528) with the use of NTG to obtain a mutant which highly produces deferriferrichrysin (Patent Document 4); a method which comprises treating *Aspergillus sojae* with ultraviolet light to obtain a white koji mutant having white conidia and obtain miso with a good color hue (Patent Document 5); a method which comprises mutagenizing *Aspergillus oryzae* with the use of, for example, X-ray to obtain a strain having a reduced isovaleraldehyde productivity for preventing the occurrence of a stuffy smell that is a deteriorated odor of sake (Patent Document 6); a method which comprises irradiating red koji mold (*Monascus*) with heavy ion beam to obtain a koji mold strain which highly producing monacolin K which is a cholesterollowering substance (Patent Document 7); a method which comprises irradiating a microorganism with iron ion beam imparting linear energy to transfer insertion mutation and deletion mutation of about 1.2 kb (Patent Document 8); an example wherein a black koji mold mutant was constructed using heavy ion beam (Non-Patent Document 2); and so on.

PRIOR ART DOCUMENTS

Patent Documents

Patent Document 1: JP-A-6-153896
Patent Document 2: JP-A-7-274944
Patent Document 3: JP-A-10-210967
Patent Document 4: JP-A-2008-054580
Patent Document 5: JP-A-7-222584
Patent Document 6: JP-A-9-70287
Patent Document 7: JP-A-2007-228849
Patent Document 8: JP-A-2008-306991

Non-Patent Documents

Non-Patent Document 1: Nature (2005) 438, 1157-61
Non-Patent Document 2: Food Sci. Technol. Res. (1999) 5(2), 153-155

SUMMARY OF THE INVENTION

Problems to be Solved by the Invention

An object of the present invention is to breed a koji mold in which the productivities of a various kinds of enzymes have been enhanced without using the genetic recombination method.

Means for Solving the Problems

To achieve the aforesaid object, the inventors of the present invention successfully obtained a koji mold having a duplication of a large-scale genomic region of 900 kb or more by mutagenizing a strain belonging to the genus *Aspergillus* (for example, *Aspergillus sojae* or *Aspergillus oryzae*) and screening a mutant in which a target gene and genes present in the neighborhood of the target gene became highly active at the same time to accomplish the present invention.

Namely, the present invention relates to the following [1] to [13].

[1] A strain belonging to the genus *Aspergillus* which has a duplication of a genome region of 900 kb or more.
[2] A strain described in [1], wherein the strain belonging to the genus *Aspergillus* is a strain belonging to *Aspergillus oryzae* or *Aspergillus sojae*.
[3] A strain described in [1] or [2], which has a duplication of a genome region of from 900 to 2,400 kb.
[4] A strain described in any of [1] to [3], which contains alkali protease gene in the duplicated genome region.
[5] A strain described in any of [1] to [4], which contains α-amylase gene in the duplicated genome region.
[6] A strain described in any of [1] to [5], which has a duplication of a genome region corresponding to the region A0090003001003-A0090003001259 of SC003 on the second chromosome in *Aspergillus oryzae* RIB40 (NRBC100959).
[7] A strain described in any of [1] to [6], which shows no reverse mutation up to at least the 10th generation in a subculture test in bran koji.
[8] A strain described in any of [1] to [7], which has a twice or more enhanced protease activity in comparison with the parent strain.
[9] A strain described in any of [1] to [8], which has a twice or more enhanced α-amylase activity in comparison with the parent strain.
[10] A strain described in any of [1] to [9], which is NITE ABP-733 (NITE BP-733) or NITE ABP-734 (NITE BP-734).
[11] A strain described in any of [1] to [10], which is obtained by mutagenesis.
[12] A soy sauce koji produced by using a strain described in any of [1] to [11].
[13] A soy sauce produced by using a soy sauce koji described in [12]. Advantage of the Invention According to the present invention, a koji mold, which highly produces various kinds of enzymes simultaneously, can be successfully obtained. The koji mold is highly useful from an industrial viewpoint since it can highly produce various kinds of enzymes at the same time. Additionally, it can be easily usable in food manufacturing, since no genetic recombination method is used. In particular, this koji mold enables high production of enzymes (proteases, etc.) decomposing various starting materials which are required in manufacturing soy sauce, which results in a remarkable increase in the utilization efficiency of the starting materials.

It is known that koji mold mutants frequently undergo reverse mutation. However, since the koji mold strain according to the present invention which has a large-scale genomic duplication and does not have a small mutation such as point mutation, it is genetically stable and scarcely undergoes reverse mutation. Thus, the yield can be markedly enhanced in comparison with conventional methods. The effect that reverse mutation is not caused is particularly superior in industrial application since, in manufacturing soy sauce, not only the utilization efficiency of the starting materials can be enhanced but also the labor for managing tane koji (mold starter) can be considerably relieved, which largely contributes to an increase in productivity.

BEST MODE FOR CARRYING OUT THE INVENTION

Exampled of the koji mold to be used in the present invention include *Aspergillus sojae, Aspergillus oryzae, Aspergillus niger, Aspergillus awamori* etc. Among them, strains belonging to *Aspergillus sojae* and *Aspergillus oryzae* are preferable.

Examples of such strains include those which have been deposited with deposit authorities and are easily available for those skilled in the art, e.g., *Aspergillus sojae* 262 (FERM P-2188), *Aspergillus sojae* 2165 (FERM P-7280), *Aspergillus sojae*(ATCC42251), *Aspergillus oryzae* (IAM2638), *Aspergillus oryzae* RIB40 (NBRC100959) etc.

Feature of the strain according to the present invention is that it has at least 2 duplicate copies of a large-scale genomic region duplication of 900 kb or more, preferably from 900 to 2,400 kb. These duplicated genome regions are either aligned on a single chromosome or located on different chromosomes separately from each other.

In manufacturing soy sauce, a koji mold, which can highly produce at the same time protease for hydrolyze proteins and producing amino acids which contribute to the body taste and amylase for producing glucose that serves as the substitute in lactic acid fermentation and yeast fermentation, is desirable. Based on the genome data of *Aspergillus oryzae* RIB40, it has been clarified that genes of these enzymes are located on the same chromosome without interposing centromere. A koji mold with stable properties which simultaneously shows high activities of these enzymes and has a duplication of a large-scale genome region can be efficiently obtained by first, selecting mutants having a protease production capability enhanced twice or more, and then further selecting, from among the mutants, a strain having an amylase activity enhanced twice or more. Although a combination of protease with amylase is described above as an example, any combination is possible as long as genes are located on the same chromosome without interposing centromere.

Figure 2:
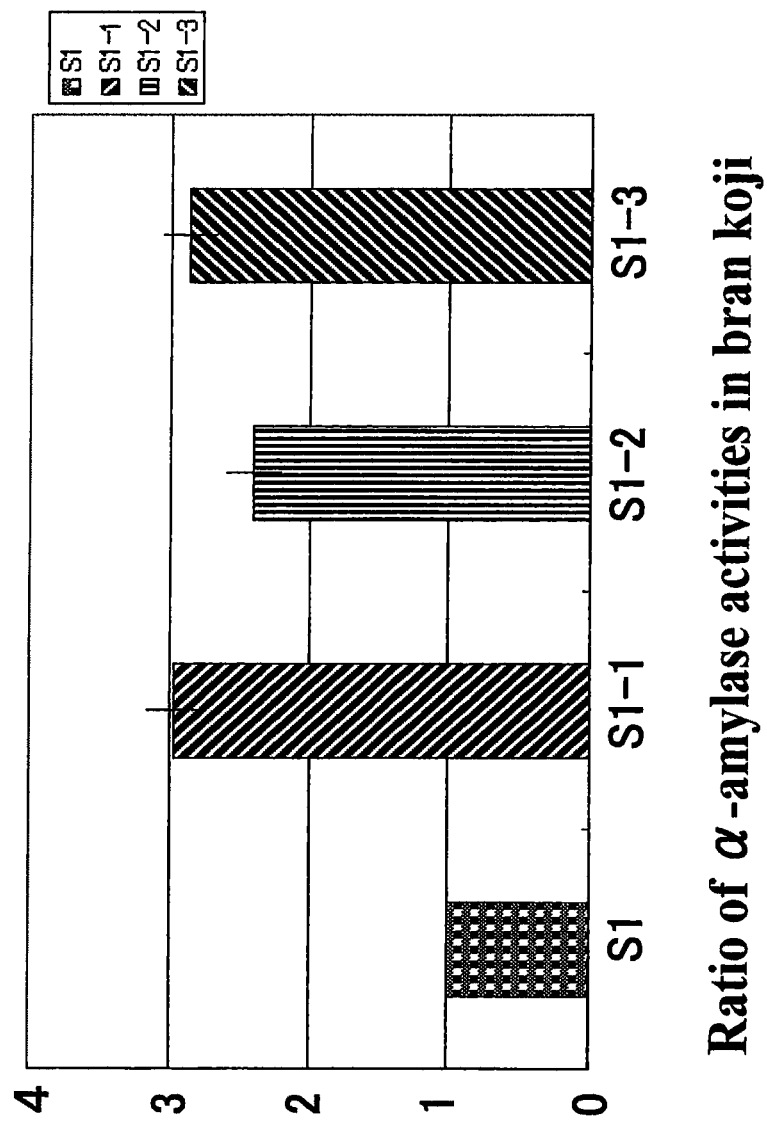
FIG. 2 shows the results of the measurement of α-amylase activities of the strains S1-1, S1-2 and S1-3 according to the present invention in bran koji.

As a typical examples of such a duplication of a large-scale genome region, the duplication derived from (corresponding to) SC003 region which contains alkali protease gene and/or α-amylase gene and is located on the second chromosome of *Aspergillus oryzae* RIB40 (NBRC100959) which has been deposited with Biological Resource Center of National Institute of Technology and Evaluation (NITE) (or National Research Institute of Brewing), can be cited. The "SC003 region" can be specified as (http://www.bio.nite.go.jp/dogan/GeneMap?GENOME_ID=ao_G2) by retrieving DOGAN (Database Of the Genomes Analyzed at NITE) (http://www.bio.nite.go.jp/dogan/Top) which is a genome analysis database provided by National Institute of Technology and Evaluation (NITE). Also, SC003 region is shown by FIG. 2 in DNA Res. 2008 August; 15(4):172-83.

Figure 9:
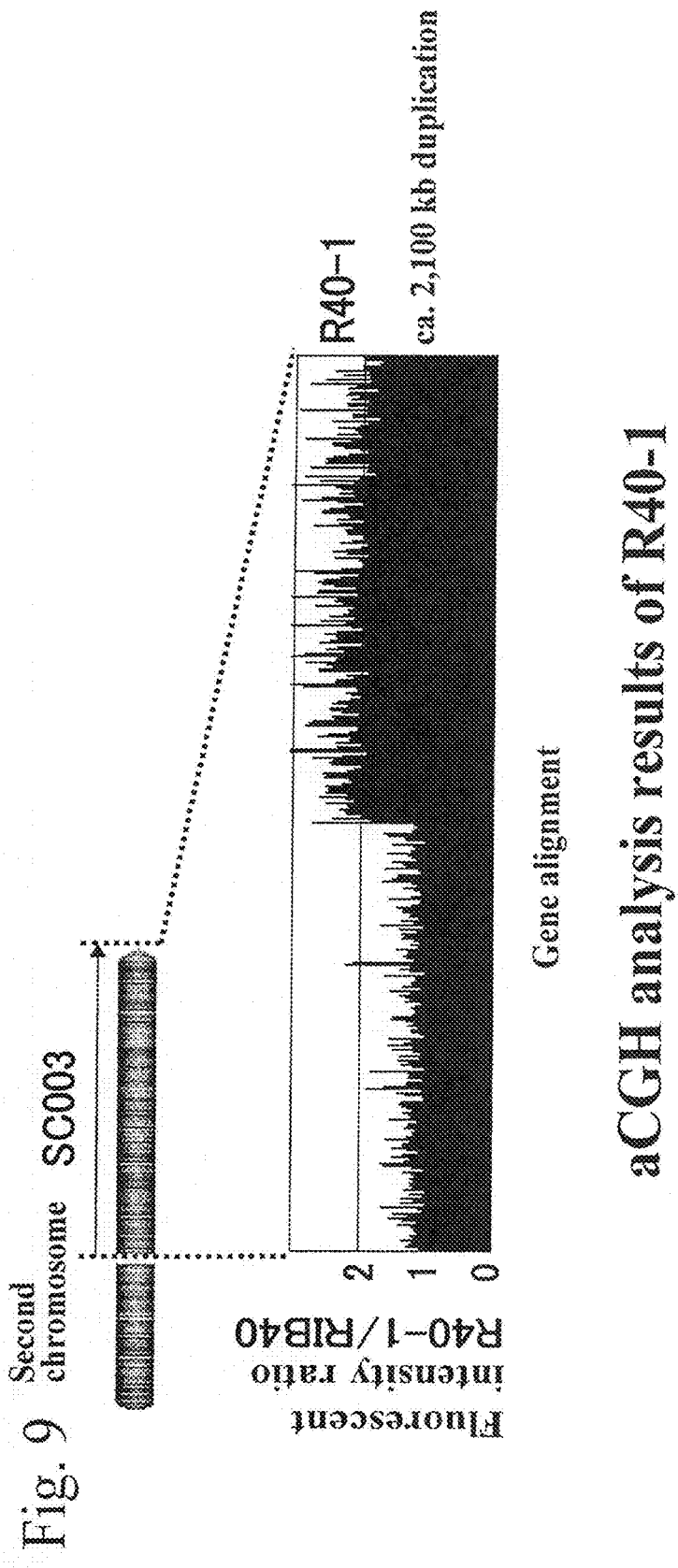
FIG. 9 shows the results of the analysis of the strain R40-1 according to the present invention by the aCGH method.

Alternatively, individual regions on the second chromosome, as will be shown in Examples hereinafter, may be cited as typical examples of the duplication of a large-scale genome region, i.e., regions containing alkali protease gene and α-amylase gene and derived from *Aspergillus sojae*, such as an about 900 kb region (corresponding to the region from A0090003000925-A0090003001259 in *Aspergillus oryzae* RIB40), an about 1,500 kb region (corresponding to the region from A0090003001003-A0090003001556 in *Aspergillus oryzae* RIB40) and an about 2,400 kb region (corresponding to the region from A0090003000654-A0090003001556 in *Aspergillus oryzae* RIB40), and a 2,100 kb region originating in *Aspergillus oryzae* RIB40 (A0090003000759-A0090003001558) (FIG. 9).

Among the regions, a region corresponding to A0090003001003-A0090003001259 of SC003 on the second chromosome in *Aspergillus oryzae* RIB40 (NRBC100959) is particularly preferable as the duplicated region to be used in the present application. The corresponding regions are not limited to those originating in *Aspergillus oryzae* RIB40 but include regions derived from strains which are usable in the present invention.

Although the strain of the present invention is not limited by the presence or absence of reverse mutation occurring in subculture, a strain which does not undergo reverse mutation is preferred. The term "reverse mutation" as used herein means a drop of the large-scale genome duplication. Whether reverse mutation is caused is determined as described below. After culturing a strain in bran koji for 4 days, the activities (herein, protease activity, amylase activity, etc.) or expression amounts of enzyme genes contained in the duplication of the strain are compared with those of the parent strain. A strain showing a twice or more increase over the parent strain is defined as that no reverse mutation was undergone, whereas a strain showing enzyme activity levels equal to or less than those of the parent strain is defined as having undergone reverse mutation. Additionally, whether a strain undergoes reverse mutation is determined as described below. In a subculture test by a conventional method using bran koji, a strain showing no reverse mutation up to at least the 10th generation is referred to as "a strain which does not undergo reverse mutation", whereas a strain which undergoes reverse mutation by the 10th generation is referred to as "a strain which undergoes reverse mutation".

The strain according to the present invention can be constructed by an arbitrary mutagenesis method known in public, such as NTG treatment or irradiation with heavy ion beam, ultraviolet light or X-ray.

In the case of using ultraviolet light irradiation, for example, about $10^6$ conidia of the aforesaid strain are smeared on a casein medium [0.4% of milk casein, 0.05% of casamino acid, 0.36% of monopotassium phosphate, 1.43% of disodium phosphate, 0.5% of magnesium sulfate, 0.002% of ferric sulfate, 2% of agar, pH 6.5] and the plate is irradiated with ultraviolet light for about 5 to about 10 minutes in a clean bench.

As an example of a method for selecting a mutagenized strain, a method of selecting a strain having high protease productivity can be cited. The method comprises inoculating a casein medium with the irradiated koji mold strains, culturing the strains at a temperature appropriate for the growth of koji molds for an appropriate period of time. After the completion of the culture, selecting strains showing a large clear zone around a colony thereof and examining the brewing properties of the strains are carried out to screen a mutant showing high protease productivity.

After the ultraviolet light irradiation, strains may be selected by, for example, the following method. The conidia are allowed to fix by culturing on the plate for 3 to 5 days at 30° C. Then, strains showing a large clear zone are selectively collected and purified by single colony isolation. The entire conidia of other strains are collected, appropriately diluted with sterilized water and then smeared on a casein plate. After culturing for 3 to 5 days at 30° C., strains showing a large clear zone are selectively collected and purified by single colony isolation.

As examples of the strains according to the present invention belonging to the genus *Aspergillus*, S1-1 strain which is described in Example 1 and R40-1 strain which is described in Example 2 were deposited on Apr. 6, 2009 with Patent Microorganism Depositary, National Institute of Technology and Evaluation (2-5-8 Kazusakamatari, Kisarazu-shi, Chiba, 292-0818 JAPAN) under deposition numbers NITE P-733 and NITE P-734. Further, request for the transfer to international deposition under the Budapest Treaty was filed to the organization and accepted as NITE ABP-733 and NITE ABP-734 respectively for S1-1 strain and R40-1 strain.

Hereinafter, the present invention will be described in detail by referring to the following Examples. However, the technical scope of the present invention is not limited thereto.

(Method for Preparing Bran Koji)

Enzyme activity of a koji mold was evaluated by a conventional method. Namely, 5 g of wheat bran, onto which 80% of water had been sprayed, was introduced into a 150 ml Erlenmeyer flask and sterilized for 50 minutes at 121° C. Then, about 2 platinum loops of the koji mold was inoculated and cultured for 4 days at 30° C. After the completion of the culture, 100 ml of sterilized water was added. Then, the flask was sealed with a rubber stopper, sufficiently shaken and allowed to stand at room temperature for 4 hours. After filtering through a No. 2 paper filter (manufactured by Advantech), the obtained extract was referred to as an enzyme sample.

(Method for Measuring Protease Activity)

The obtained enzyme sample was appropriately diluted and the measurement was carried out in accordance with the following method described in "Shoyu Shiken-Ho (Methods for Testing Soy Sauce)" (Japan Soy Sauce Laboratory, 1985, p. 287). In distilled water, 100 mg of L-tyrosine of the special grade was dissolved to give a total volume of 1 L. Into 10 ml measuring flasks, 1, 2, 3, 4 and 5 ml of the solution were introduced and distilled water was added to become 10 ml to obtain standard tyrosine solutions of 10, 20, 30, 40 and 50 µg/ml respectively. Into a test tube, 2 ml of the standard tyrosine solutions were each introduced and 5 ml of a 0.55 M sodium carbonate solution and 1 ml of Folin reagent diluted to 3-fold were added. After maintaining at 30° C. for 30 minutes in a thermostatic water tank, the absorbance was measured at 660 nm with a spectrophotometer. As a control cell, distilled water was used and subjected to the same procedure. Thus, a standard curve was drawn by referring the abscissa to the tyrosine content (µg) and the ordinate to the absorbance at 660 nm. The aforesaid enzyme sample was appropriately diluted and a 1 ml thereof was mixed with 1 ml of a 1.5% milk casein solution. After reacting for 10 minutes at 30° C., the reaction was stopped by adding 3 ml of a 0.4 M trichloroacetic acid solution. Then the reaction mixture was allowed to stand at 30° C. for 30 minutes in a thermostatic water tank, and the precipitate thus formed was filtered through a No. 2 paper filter (manufactured by Advantech). Into a test tube, 2 ml of the filtrate was introduced and the absorbance was measured at 660 nm. As a blank, 3 ml of a 0.4 M trichloroacetic acid solution was added before adding the enzyme and the same procedure was conducted. The difference obtained by subtracting the absorbance of the blank from the absorbance of the sample was referred to as ΔE. Then, the amount of tyrosine was determined from the standard curve and ΔE. The amount of the enzyme which can release a non-proteinous substance corresponding to 1 µg of tyrosine in 1 minutes was referred to as 1 U (unit) and the value per gram of the bran koji was calculated.

(Method for Measuring α-Amylase Activity)

The obtained enzyme sample was appropriately diluted. Using an α-amylase assay kit (Kikkoman Brewing Analysis Kit code: 60213), measurement was carried out in accordance with the protocol attached to the kit. α-Amylase activity was expressed by referring the titer which can release 1 µmol of 2-chloro-4-nitrophenol within 1 minute per gram of the bran koji as to 1 U (unit).

(Method for Measuring CMCase Activity)

Carboxymethyl cellulose (CMC) was used as a substrate and detection was carried out by the dinitrosalicylic acid (DNS) method. In 60 ml of distilled water, 1.0 g of the substrate was dissolved and adjusted to pH 4.8 with 0.4 M acetic acid. Next, 25 ml of a 0.4 M acetate buffer solution (pH 4.8) was added and the total volume was adjusted to 100 ml with distilled water to obtain a 1% substrate solution. To this 1% substrate solution, the equivalent amount of the enzyme sample was added and reaction for 1 hour at 40° C. is carried out. After stopping the reaction by heating to 100° C. for 10 minutes, 0.75 ml of the liquid reaction mixture was taken into a test tube. Thereto, 0.75 ml of DNS reagent was added and the mixture was well shaken. Next, the test tube was sealed with a glass stopper and boiled for 7 minutes. After cooling, 3 ml of distilled water was added and the absorbance was measured at 535 nm. The amount of the enzyme which can release reducing sugar in an amount corresponding to 1 mg of glucose within 1 minute was referred to as 1 U (unit).

Example 1

Conidia of S1 strain belonging to *Aspergillus sojae* (owned by Kikkoman Corporation) were subjected to the mutagenesis by irradiating with ultraviolet light in the aforesaid manner or one of the publicly known mutagenesis treatments other than ultraviolet light irradiation. Then, the conidia were smeared on a casein medium and screening was conducted depending on clear zone size. Strains showing a clear zone 1.5 times or more larger than that of the parent strain were cultured in bran koji for 4 days at 30° C. and named respectively S1-1, S1-2 and S1-3. S1-1 was a strain obtained by the mutagenesis via ultraviolet light irradiation, while S1-2 and S1-3 were strains obtained by publicly known mutagenesis treatments other than ultraviolet light irradiation. Each strain was subjected to the protease activity measurement by the aforesaid measurement method. As the results of the measurement, S1-1, S1-2 and S1-3 each showed a protease activity and an α-amylase activity twice or more higher than those of the parent strain.

Figure 1:
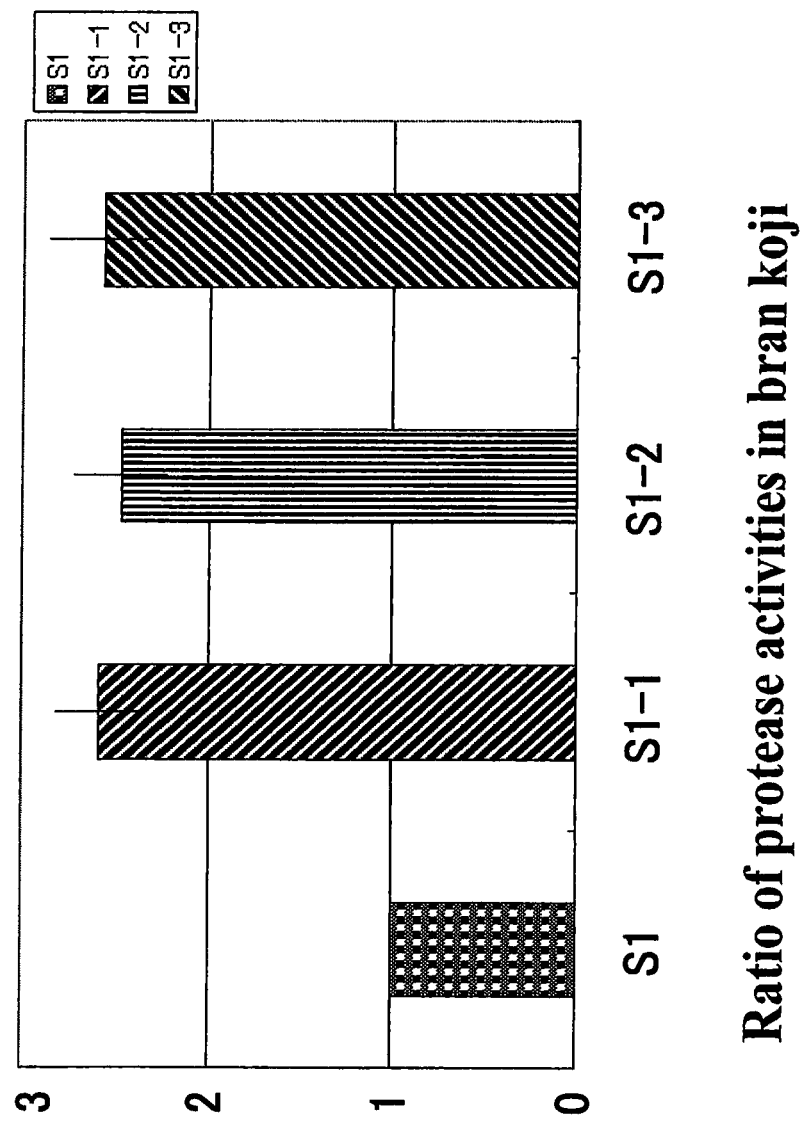
FIG. 1 shows the results of the measurement of protease activities of strains S1-1, S1-2 and S1-3 according to the present invention in fusuma koji (bran koji).

FIG. 1 shows the results of the protease activity measurement of the each mutant strain in bran koji.

FIG. 2 shows the results of the α-amylase activity measurement of the each mutant strain in bran koji.

Example 2

Conidia of *Aspergillus oryzae* RIB40 (NBRC100959) were mutagenized by irradiating with ultraviolet light in the same manner as described above. Then, thes conidia were smeared on a casein medium and screening was carried out depending on clear zone size, as in Example 1. A strain showing a clear zone of 1.5 times or more larger than that of the parent strain was cultured in bran koji for 4 days at 30° C. and named R40-1 strain, Next, the protease activity was measured by the aforesaid measurement method. As the results of the measurement, R40-1 strain showed a protease activity and an α-amylase activity twice or more higher than those of the parent strain.

Figure 3:
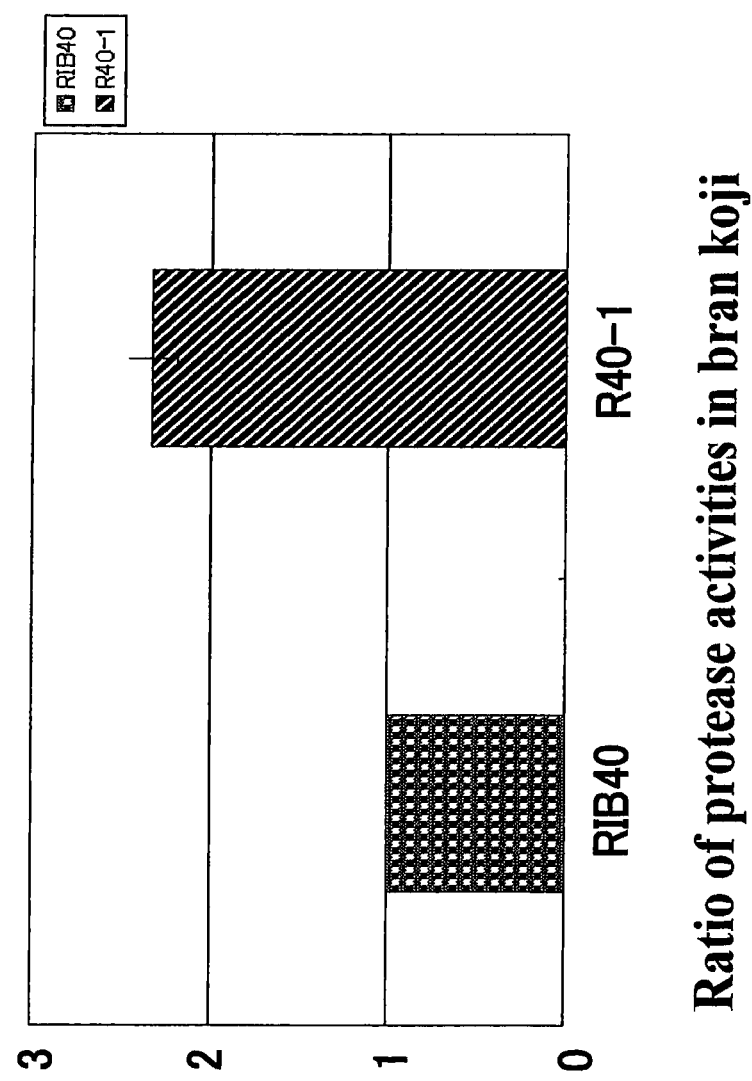
FIG. 3 shows the results of the measurement of protease activity of a strain R40-1 according to the present invention in bran koji.

FIG. 3 shows the results of the protease activity measurement of the obtained mutant strain in bran koji.

Figure 4:
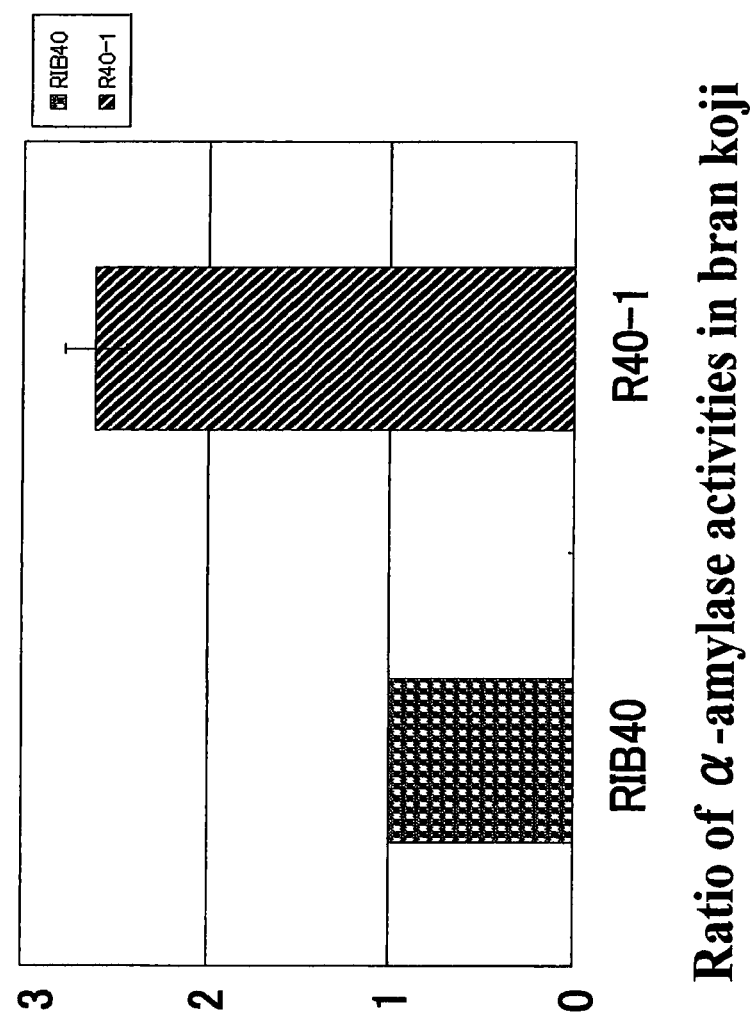
FIG. 4 shows the results of the measurement of α-amylase activity of the strain R40-1 according to the present invention in bran koji.

FIG. 4 shows the results of the α-amylase activity measurement of the obtained in mutant strain in bran koji.

Example 3

Figure 5:
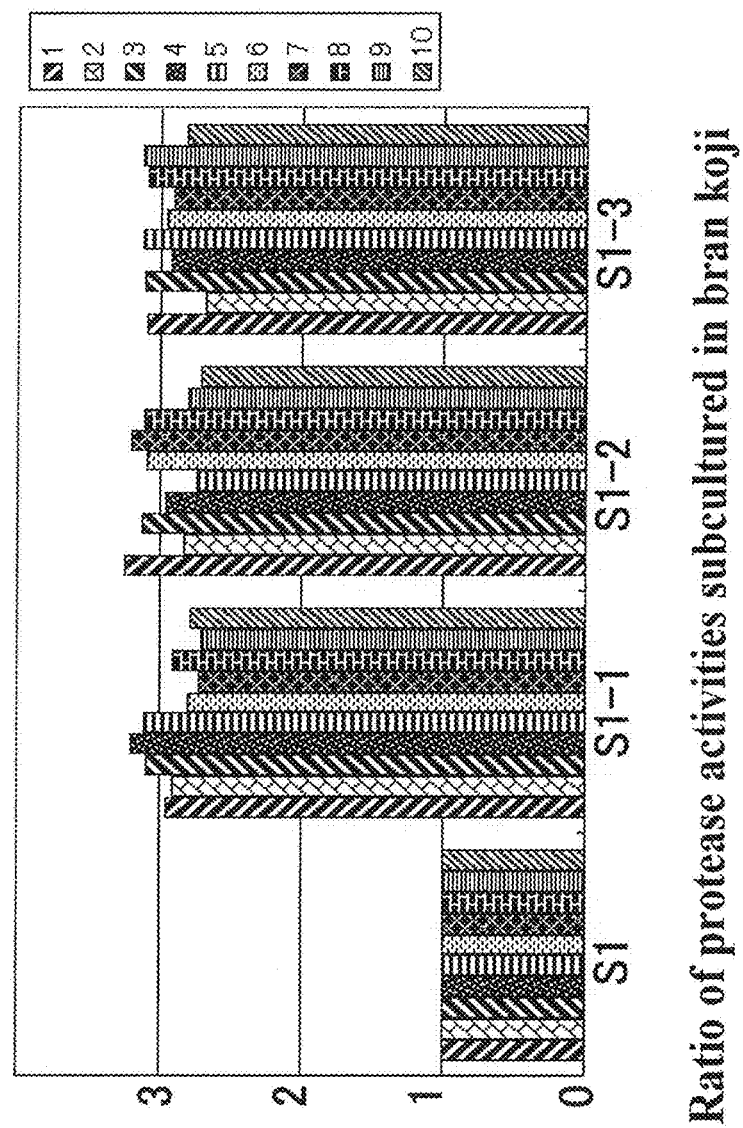
FIG. 5 shows the results of the measurement of protease activities of the strains S1-1, S1-2 and S1-3 according to the present invention in a subculture test in bran koji.

Furthermore, the obtained mutants S1-1, S1-2 and 51-3 were subjected to a subculture test in bran koji and the protease activities were measured in accordance with the above measurement method (FIG. 5). As FIG. 5 clearly shows, all of the obtained mutants stably showed (twice or more) higher protease activities than that of the parent strain up to the 10th generation, indicating that the strains had not undergone reverse mutation.

Example 4

Manufacturing of Soy Sauce Koji

Figure 6:
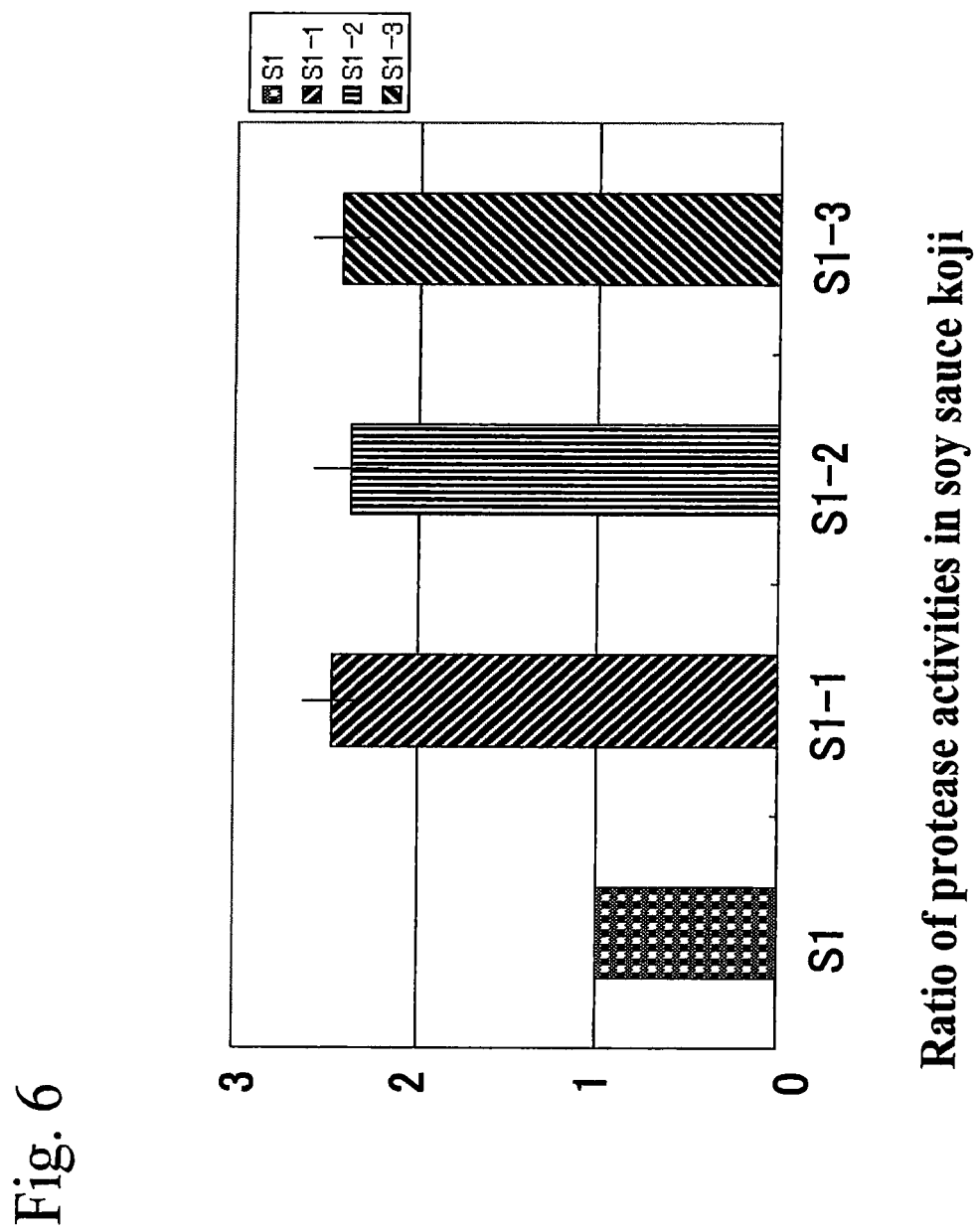
FIG. 6 shows the results of the measurement of protease activities of the strains S1-1, S1-2 and S1-3 according to the present invention in say sauce koji.

To a mixture of cooked and defatted soybeans with roasted and milled wheat grains, 0.1% (w/w) of each of the above strains was added as a mold starter and the resultant mixture was subjected to koji-making over 3 days. Then, the protease activity of the obtained soy sauce koji was measured in accordance with the above measurement method (FIG. 6). As FIG. 6 clearly shows, all of S1-1, S1-2 and S1-3 showed twice or more higher protease activities than that of the parent strain.

Example 5

The koji digestion levels of the aforesaid soy sauce koji were measured in accordance with the following method described in "Shoyu Shiken-Ho (Methods for Testing Soy Sauce)" (Japan Soy Sauce Laboratory, 1985, p. 104).

Figure 7:
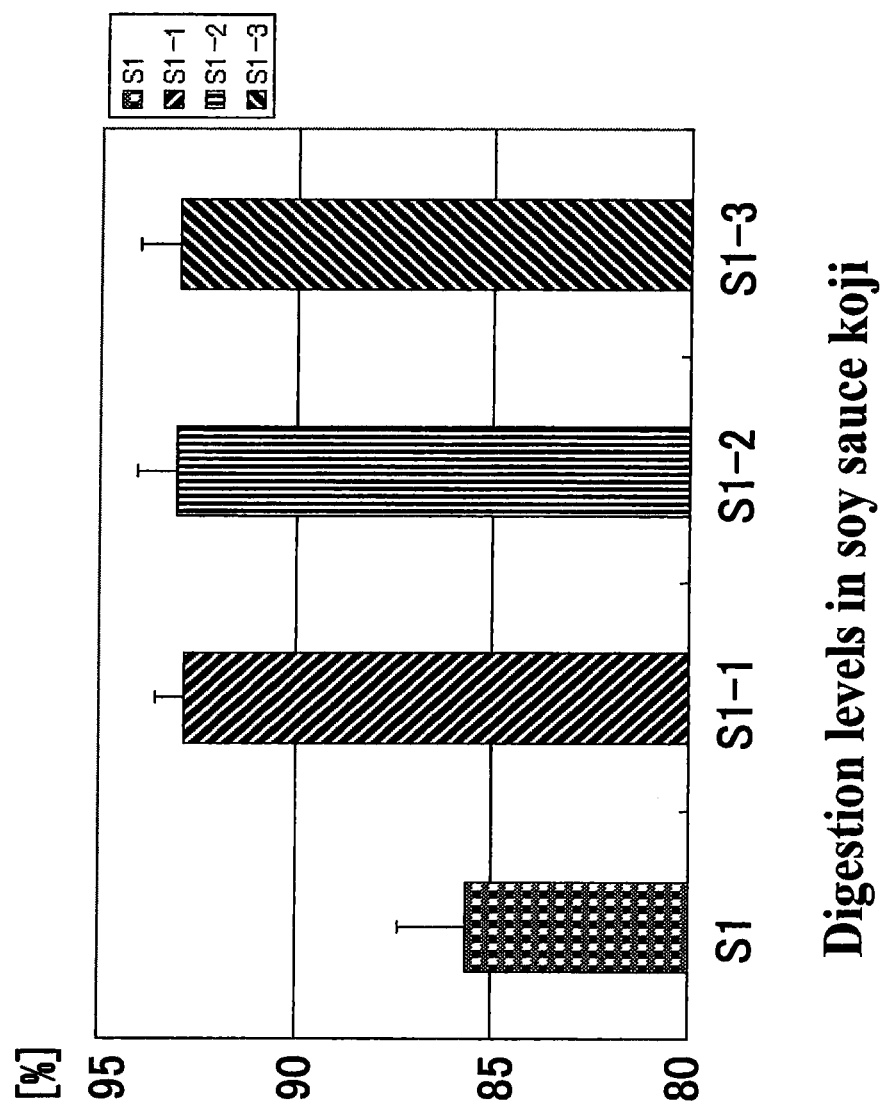
FIG. 7 shows the results of the measurement of koji digestion levels of the strains S1-1, S1-2 and S1-3 according to the present invention in say sauce koji.

The koji digestion levels of the soy sauce koji were measured as described below. Into a 500 ml Erlenmeyer flask, 100 g of each soy sauce koji was taken and 200 ml of a 18.5% aqueous sodium chloride solution was added thereto. The flask was sealed with a cork stopper and then autodigestion was carried out for 1 week at 37° C. During the period, the mixture in the flask was stirred once every day. The moromi (mash) thus digested was homogeneously mixed in a mixer and the total nitrogen content and sodium chloride content of the moromi were measured. Further, the homogenized moromi was filtered and the total nitrogen content and sodium chloride content of the filtrate were measured too. From the measurement data, the digestion level was determined in accordance with the following formula (FIG. 7). As FIG. 7 clearly shows, all of S1-1, S1-2 and S1-3 showed higher digestion levels than strain S1, i.e., the parent strain. Improvement in the koji digestion level directly results in an increase in the utilization efficiency of the starting materials in manufacturing soy sauce.

Koji digestion level (%)=[(NaCl content % in moromi)/(total N content % in moromi)]×[(N content % in liquor)/(NaCl content % in liquor)]×100

Example 6

Figure 8:
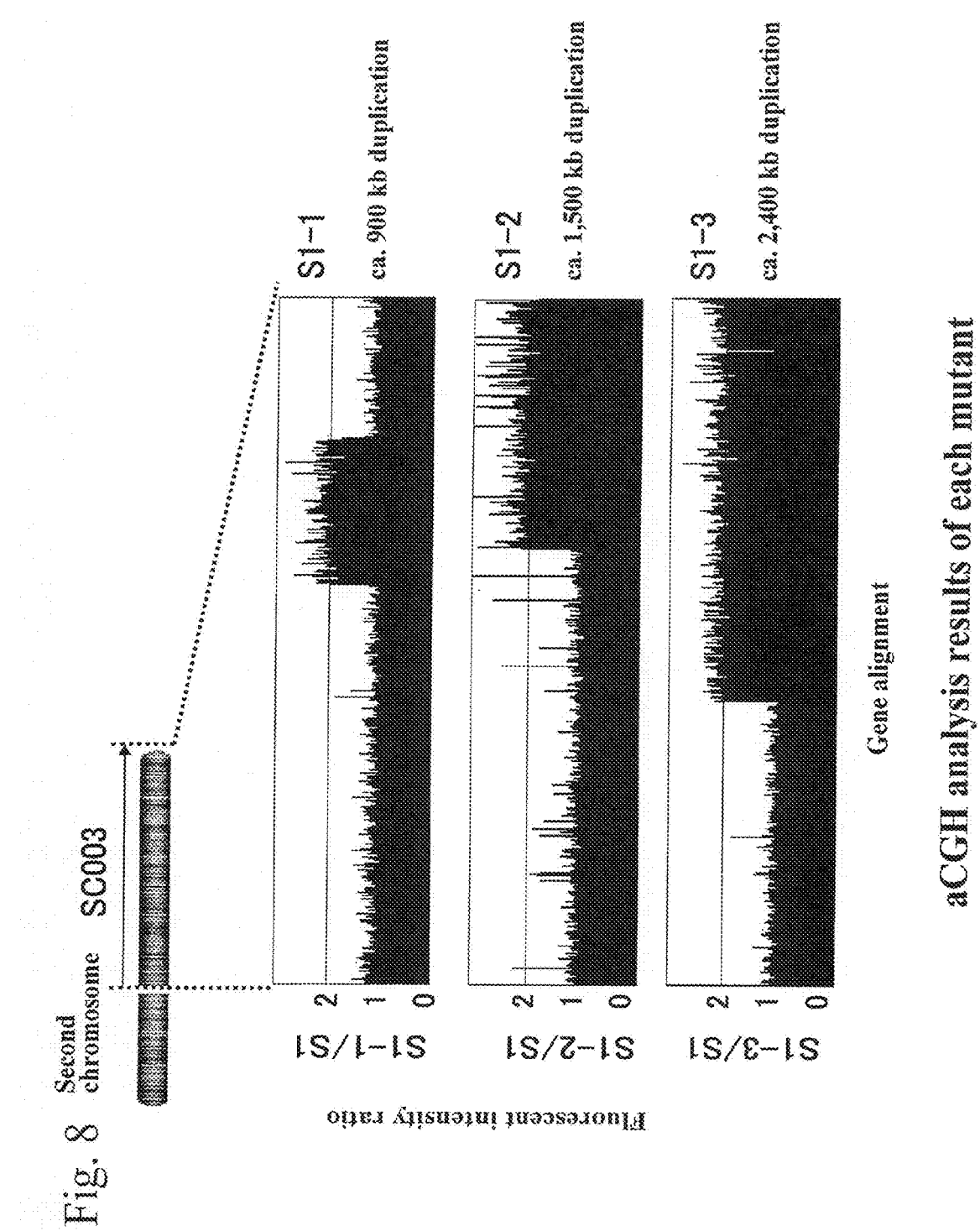
FIG. 8 shows the results of the analysis of the strains S1-1, 81-2 and S1-3 according to the present invention by the array comparative genomic hybridization method (hereinafter referred to as aCGH method) using a microarray.

Analysis by Array Comparative Genomic Hybridization Method (aCGH Method) Using Microarray By using a microarray (Agilent Technologies), gene copy number variation of S1-1 strain was comprehensively analyzed by the aCGH method. As a result, it was found that genes present in an about 900 kb region (corresponding to A0090003000925-A0090003001259 in *Aspergillus oryzae* RIB40) containing alkali protease gene and α-amylase gene were increased twice or more in comparison with the parent strain, which indicated that S1-1 strain had a large-scale genome duplication. Other protease-high-producing strains were also analyzed by aCGH. As a result, it was found that 51-2 had a large-scale genome duplication of an about 1,500 kb region (corresponding to A0090003001003-A0090003001556 region in *Aspergillus oryzae* RIB40) and S1-3 had a large-scale genome duplication of an about 2,400 kb region (corresponding to A0090003000654-A0090003001556 in *Aspergillus oryzae* RIB40), each region containing alkali protease gene and α-amylase gene (FIG. 8).

Similarly, R40-1 strain obtained in Example 2 was analyzed by the aCGH method. As a result, it was found that the strain had a large-scale genome duplication of an about 2,100 kb region (A0090003000759-A0090003001558) containing alkali protease gene and α-amylase gene similar to S1-1 strain (FIG. 9).

Example 7

Alkali Protease Gene Copy Number Validation Analysis by Quantitative PCR Method

Figure 10:
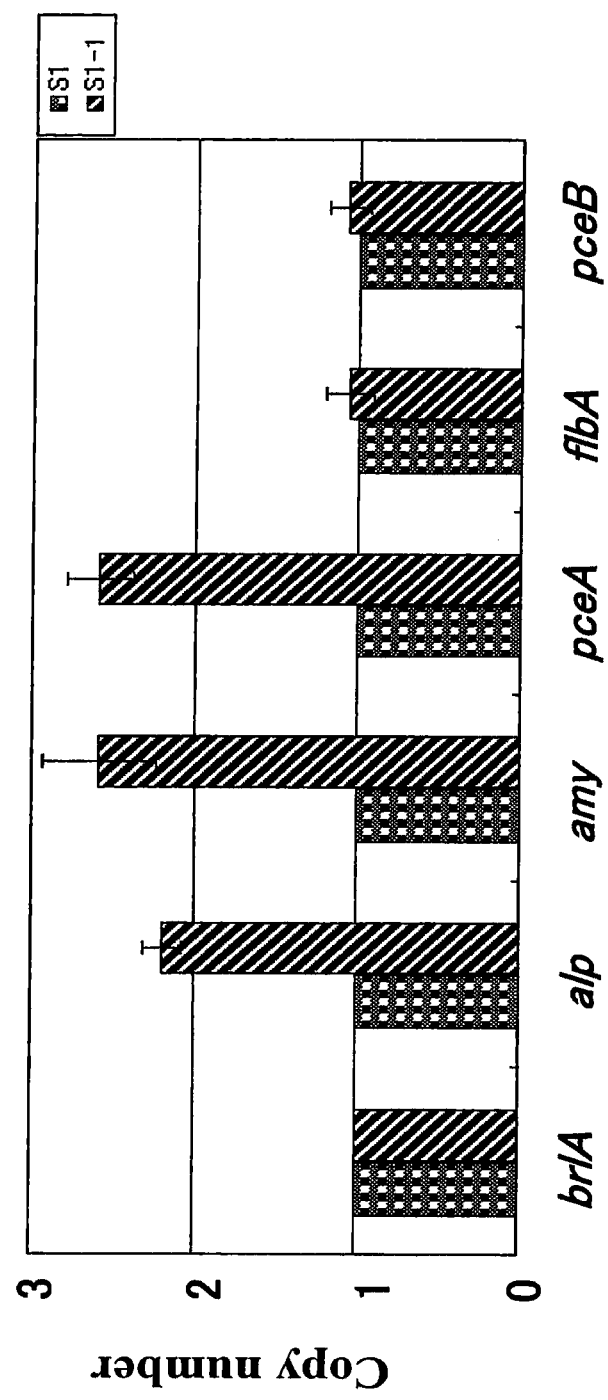
FIG. 10 shows the results of the gene copy number validation analysis of the strain S1-1 according to the present invention by the quantitative PCR method.

The gene copy numbers of the each gene in the duplicated region of S1-1 strain were quantified by the quantitative PCR method and compared with those in the parent strain S1 (M×3000P, Stratagene) (FIG. 10). The PCR was conducted for 40 cycles with each cycle consisting of 10 seconds at 95° C., 20 seconds at 60° C. and 15 seconds at 72° C. As control genes, brlA gene in the first chromosome, flbA gene in the third chromosome and pceB gene in the fourth chromosome were used. As FIG. 10 clearly shows, S1-1 strain has each of alkali protease gene (alp), amylase gene (amy) and pceA gene, which are present in the about 900 kb region which have confirmed as duplicated by the aCGH method, in an amount twice as much as the parent strain S1, by which the analysis results by the aCGH method was confirmed. The base sequences of the primers used are described below (Table 1), i.e., brlA-F (SEQ ID NO:1), brlA-R (SEQ ID NO:2), alp-F (SEQ ID NO:3), alp-R (SEQ ID NO:4), amy-F (SEQ ID NO:5), amy-R (SEQ ID NO:6), pceA-F (SEQ ID NO:7), pceA-R (SEQ ID NO:8), flbA-F (SEQ ID NO:9), flbA-R (SEQ ID NO:10), pceB-F (SEQ ID NO:11) and pceB-R (SEQ ID NO:12). The primer sequences may be used not only for *Aspergillus sojae* but also for various gene copies in the duplicated regions in strains which can be used in the present application.

TABLE 1

Primer sequences for quantitative PCR

| target | name | sequence (5'-3') |
|--------|------|------------------|
| brlA | brlA-F | TATGCCCGACTTTCTGTCCG |
|      | brlA-R | ATGGGAGGCTGTGTGTTCCA |
| alp  | alp-F  | CAGGCGGTGGCTACTCTAAG |
|      | alp-R  | CTCTTCTGGATAGCGGCAAC |
| amy  | amy-F  | GGCACTGCAGATGACTTGAAGG |
|      | amy-R  | CCCGCTCCATCATAGCCCTG |
| pceA | pceA-F | GGAGCGCATCAAGAACAAGAT |
|      | pceA-R | ATGTCATAGCCAAGCTGCGG |

TABLE 1-continued

Primer sequences for quantitative PCR

| target | name | sequence (5'-3') |
|---|---|---|
| flbA | flbA-F | CAATCTCTCGGCCATTGGAG |
|  | flbA-R | CGCTGACTTGGGAGAGCTTG |
| pceB | pceB-F | AGCTTGACTGGACGGAGCC |
|  | pceB-R | CAGGGCGGTAATGATCTTGG |

Example 8

Figure 11:
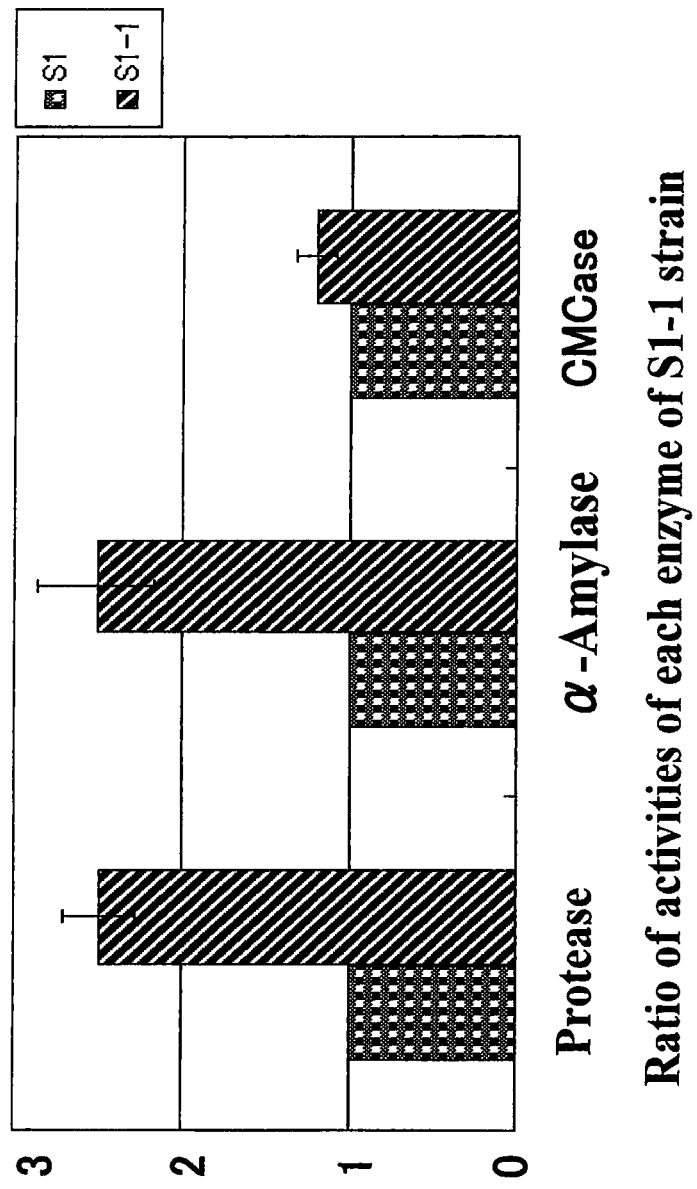
FIG. 11 shows the results of the measurement of enzymatic activities of an enzyme which corresponds to the duplicated region of the strain S1-1 according to the present invention in bran koji and another enzyme which does not correspond thereto.

Using S1-1 strain, bran koji was prepared and the activities of the individual enzymes were measured by the aforesaid methods. As a result, the activities of the enzymes (protease and α-amylase) encoded by the genes contained in the genome duplication were significantly i.e., twice or more enhanced in comparison with those of the parent strain, while the activity of carboxymethyl cellulase (CMCase) which is not contained in the aforesaid region showed no significant change (FIG. 11). The results indicated that the increases in the protease and α-amylase activities depended on the duplication.

Although the present invention has been described in detail by referring to specific examples, it will be understood by those skilled in the art that various modifications or alterations may be made without departing from the spirit and scope of the present invention.

The present application is based on Japanese Patent Application filed on Apr. 17, 2009 (Japanese Patent Application 2009-100645) and the disclosure thereof is included herein by reference.

INDUSTRIAL APPLICABILITY

By inoculating the strain according to the present invention belonging to the genus *Aspergillus* to a starting material of soy sauce and culturing, a solid koji or a liquid koji having an improved ability of producing a variety of enzymes can be obtained. Soy sauce is produced with mash using the koji. By inoculating the strain according to the present invention to a starting rice material and culturing, mirin, mirin-like products and sake can be produced. By liquid-culturing the strain according to the present invention, furthermore, a seasoning liquor comprising digested gluten can be produced. Accordingly, the present invention relates to such production methods and various foods such as soy sauce which are produced thereby.

SEQUENCE LISTING FREE TEXT

SEQ ID NO:1 represents the sequence of a primer for brlA gene.
SEQ ID NO:2 represents the sequence of a primer for brlA gene.
SEQ ID NO:3 represents the sequence of a primer for alp gene.
SEQ ID NO:4 represents the sequence of a primer for alp gene.
SEQ ID NO:5 represents the sequence of a primer for amy gene.
SEQ ID NO:6 represents the sequence of a primer for amy gene.
SEQ ID NO:7 represents the sequence of a primer for pceA gene.
SEQ ID NO:8 represents the sequence of a primer for pceA gene.
SEQ ID NO:9 represents the sequence of a primer for flbA gene.
SEQ ID NO:10 represents the sequence of a primer for flbA gene.
SEQ ID NO:11 represents the sequence of a primer for pceB-gene.
SEQ ID NO:12 represents the sequence of a primer for pceB-gene.

The invention claimed is:

1. A strain belonging to *Aspergillus oryzae* or *Aspergillus sojae* having a duplication of a genome region that consists of a genome region corresponding to the region A00900003001003-A00900003001259 of SC003 on the second chromosome of *Aspergillus oryzae* RIB40 (NBRC100959) and wherein the strain is characterized by at least a two-fold increase in protease activity and at least a two-fold increase in α-amylase activity.

2. The strain of claim 1, which is obtained by mutagenesis treatment carried out on a strain belonging to the genus *Aspergillus*.

3. A soy sauce koji produced by using the strain of claim 1.

4. A soy sauce produced by using the soy sauce koji of claim 3.

5. The strain of claim 1, having a duplication of a genome region of from 900 to 2,400 kb.

6. A soy sauce koji produced by using the strain of claim 5.

7. A soy sauce produced by using the soy sauce koji of claim 6.

8. The strain of claim 1, which contains alkali protease gene in the duplicated genome region.

9. A soy sauce koji produced by using the strain of the strain of claim 8.

10. A soy sauce produced by using the soy sauce koji of claim 9.

11. The strain of claim 1, which contains a-amylase gene in the duplicated genome region.

12. A soy sauce koji produced by using the strain of claim 11.

13. A soy sauce produced by using the soy sauce koji of claim 12.

14. The strain of claim 1, which shows no reverse mutation up to at least the 10th generation in a subculture test in bran koji.

15. A soy sauce koji produced by using the strain of claim 14.

16. A soy sauce produced by using the soy sauce koji of claim 15.

17. The strain of claim 14, which is NITE BP-733 or NITE BP-734.

18. A soy sauce koji produced by using the strain of claim 17.

19. A soy sauce produced by using the soy sauce koji of claim 18.

* * * * *

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Primer Sequence

<400> SEQUENCE: 1
tatgcccgac tttctgtccg                                                    20

<210> SEQ ID NO 2
<211> LENGTH: 20
<212> TYPE: DNA
<213> ORGANISM: Artificial Sequence
<220> FEATURE:
<223> OTHER INFORMATION: Primer Sequence

<400> SEQUENCE: 2
atgggaggct gtgtgttcca                                                    20

<210> SEQ ID NO 3
<211> LENGTH: 20
<212> TYPE: DNA
```

```
<213> ORGANISM: Artificial Sequence
<220> FEATURE:
<223> OTHER INFORMATION: Primer Sequence

<400> SEQUENCE: 3
caggcggtgg ctactctaag                                              20

<210> SEQ ID NO 4
<211> LENGTH: 20
<212> TYPE: DNA
<213> ORGANISM: Artificial Sequence
<220> FEATURE:
<223> OTHER INFORMATION: Primer Sequence

<400> SEQUENCE: 4
ctcttctgga tagcggcaac                                              20

<210> SEQ ID NO 5
<211> LENGTH: 22
<212> TYPE: DNA
<213> ORGANISM: Artificial Sequence
<220> FEATURE:
<223> OTHER INFORMATION: Primer Sequence

<400> SEQUENCE: 5
ggcactgcag atgacttgaa gg                                           22

<210> SEQ ID NO 6
<211> LENGTH: 20
<212> TYPE: DNA
<213> ORGANISM: Artificial Sequence
<220> FEATURE:
<223> OTHER INFORMATION: Primer Sequence

<400> SEQUENCE: 6
cccgctccat catagccctg                                              20

<210> SEQ ID NO 7
<211> LENGTH: 21
<212> TYPE: DNA
<213> ORGANISM: Artificial Sequence
<220> FEATURE:
<223> OTHER INFORMATION: Primer Sequence

<400> SEQUENCE: 7
ggagcgcatc aagaacaaga t                                            21

<210> SEQ ID NO 8
<211> LENGTH: 20
<212> TYPE: DNA
<213> ORGANISM: Artificial Sequence
<220> FEATURE:
<223> OTHER INFORMATION: Primer Sequence

<400> SEQUENCE: 8
atgtcatagc caagctgcgg                                              20

<210> SEQ ID NO 9
<211> LENGTH: 20
<212> TYPE: DNA
<213> ORGANISM: Artificial Sequence
<220> FEATURE:
<223> OTHER INFORMATION: Primer Sequence

<400> SEQUENCE: 9
caatctctcg gccattggag                                              20
```

```
<210> SEQ ID NO 10
<211> LENGTH: 20
<212> TYPE: DNA
<213> ORGANISM: Artificial Sequence
<220> FEATURE:
<223> OTHER INFORMATION: Primer Sequence

<400> SEQUENCE: 10
cgctgacttg ggagagcttg                                               20

<210> SEQ ID NO 11
<211> LENGTH: 19
<212> TYPE: DNA
<213> ORGANISM: Artificial Sequence
<220> FEATURE:
<223> OTHER INFORMATION: Primer Sequence

<400> SEQUENCE: 11
agcttgactg gacggagcc                                                19

<210> SEQ ID NO 12
<211> LENGTH: 20
<212> TYPE: DNA
<213> ORGANISM: Artificial Sequence
<220> FEATURE:
<223> OTHER INFORMATION: Primer Sequence

<400> SEQUENCE: 12
cagggcggta atgatcttgg                                               20
```